United States Patent
Sakuma et al.

(12)
(10) Patent No.: US 6,221,931 B1
(45) Date of Patent: Apr. 24, 2001

(54) DENTAL RESTORATIVE COMPOSITION

(75) Inventors: Tetsuro Sakuma; Makoto Katsu; Takayuki Ueno; Norikazu Nakagaki; Tomohiro Kumagai, all of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/375,508

(22) Filed: Aug. 17, 1999

(30) Foreign Application Priority Data

Sep. 2, 1998 (JP) .................................................. 10-248356

(51) Int. Cl.[7] ............................ A61K 6/083; A61K 6/09; C08K 3/36; C08L 33/14; C08L 33/06
(52) U.S. Cl. ...................... 523/116; 523/220; 524/493; 524/494; 524/560; 428/404
(58) Field of Search .................................. 523/116, 220; 524/493, 494, 560; 428/404

(56) References Cited

U.S. PATENT DOCUMENTS

| | | |
|---|---|---|
| 4,771,084 | 9/1988 | Kubota et al. . |
| 4,804,690 | 2/1989 | Kubota et al. . |
| 4,820,744 | 4/1989 | Kubota et al. . |
| 4,843,110 | 6/1989 | Kubota et al. . |
| 5,043,361 | 8/1991 | Kubota et al. . |
| 5,127,834 * | 7/1992 | Hasegawa et al. . |
| 5,250,641 | 10/1993 | Kumagai et al. . |
| 5,288,341 | 2/1994 | Kojima et al. . |
| 5,290,172 | 3/1994 | Sakuma et al. . |
| 5,356,951 | 10/1994 | Yearn et al. . |
| 5,364,890 | 11/1994 | Sakuma et al. . |
| 5,407,973 | 4/1995 | Hasegawa et al. . |
| 5,456,602 | 10/1995 | Sakuma . |
| 5,739,231 | 4/1998 | Imai et al. . |
| 5,770,638 | 6/1998 | Ueno et al. . |
| 5,990,195 * | 11/1999 | Arita . |

OTHER PUBLICATIONS

U.S. application No. 09/010,856, filed Jan. 23, 1998, pending.
U.S. application No. 09/375,508, filed Aug. 17, 1999, pending.
U.S. application No. 09/375,508, filed Aug. 17, 1999, pending.
U.S. application No. 09/517,454, filed Apr. 2, 2000, pending.

* cited by examiner

Primary Examiner—Peter A. Szekely
(74) Attorney, Agent, or Firm—Oblon, Spivak, McClelland, Maier & Neustadt, P.C.

(57) ABSTRACT

A dental restorative composition is disclosed, comprising: (a) a methacrylate or acrylate monomer, (b) an organic-inorganic composite filler prepared by curing a mixture of a particulate filler having a mean particle size of 20 nm or less with a methacrylate or acrylate monomer having a viscosity of 60 cP or more and pulverizing the cured mixture, (c) a particulate filler having a mean particle size of 20 nm or less, and (d) a polymerization initiator, and further, if desired, (e) a glass powder having a maximum particle size of 5 $\mu$m or less and having a mean particle size of from 0.5 to 2 $\mu$m. The dental restorative composition according to the invention gives restorations having surface smoothness and transparency similar to natural teeth, having superior esthetics and superior physical properties such as bending strength and bending strain energy characteristics, and being provided with easy polishing.

8 Claims, No Drawings

DENTAL RESTORATIVE COMPOSITION

BACKGROUND OF THE INVENTION

1. Field of the Invention:

The present invention relates to a dental restorative composition from which restorations having surface smoothness and transparency similar to natural teeth, having superior esthetics and superior physical properties such as bending strength and bending strain energy characteristics, and being provided with easy polishing properties can be obtained.

2. Description of the Related Art:

Dental restorative compositions are basically constructed by a combination of a polymerizable monomer, a filler, and a polymerization initiator. In order to impart capacities close to natural teeth, various improvements have been made.

Hitherto, inorganic powders having a maximum particle size of from 10 to 50 μm were used as the filler of dental restorative compositions. However, in case where such filler having a relatively large particle size is used, a surface of the resulting restoration is rough and a finished surface having smoothness similar to natural teeth could not be obtained in the clinical use.

Then, as a dental restorative composition intended to compensate this defect and to improve the surface smoothness, a dental restorative composition using particulate inorganic powders having a mean particle size of from 5 to 50 nm was developed. However, since this particulate inorganic filler has a relative large specific surface area, a large amount of the monomer should be used in the dental restorative composition. Accordingly, the proportion that the filler accounts for in the composition is low as from 30 to 60% by weight, resulting in increasing the polymerization shrinkage. Thus, the resulting restoration tended to be inferior in the physical properties.

As a means for compensating this polymerization shrinkage, an organic-inorganic composite filler prepared by curing a mixture of the monomer with a particulate inorganic powder having a mean particle size of from 5 to 50 nm and pulverizing the cured mixture. Since a dental restorative composition having this organic-inorganic composite filler compounded therewith is suppressed in the specific surface area, the amount of the monomer to be compounded can be small. Accordingly, this dental restorative composition has such characteristics that it compensates the polymerization shrinkage and that the surface smoothness of the resulting restoration is superior. However, the binding between a surface of the organic-inorganic composite filler and the matrix is weak. Thus, the resulting restoration tended to be inferior in the physical properties.

In addition, in recent years, a dental restorative composition using, as a filler, a glass powder having a maximum particle size of about 2 μm was developed. Although a restoration obtained by using this dental restorative composition has clinically superior surface smoothness, it has a high surface hardness. For this reason, it is difficult to achieve the polishing, so that it requires a lot of skill to obtain a smooth surface. Also, since in this dental restorative composition, the proportion that the glass powder accounts for is relatively high, though the resulting restoration has a high bending strength, it is low in bending energy and has brittle properties, leading to problems from the clinical point of view, such as marginal fracture.

SUMMARY OF THE INVENTION

An object of this invention is to overcome the above-described defects of the conventional dental restorative compositions and to provide a dental restorative composition from which restorations having surface smoothness and transparency similar to natural teeth, having superior esthetics and superior physical properties such as bending strength and bending strain energy characteristics, and being provided with easy polishing properties can be obtained.

In order to achieve the above-described object, we, the present inventors made extensive and intensive investigations. As a result, it has been found that a dental restorative composition which fulfills the above-described object can be obtained by combining a novel organic-inorganic composite filler with a particulate filler as the filler to be used in the dental restorative composition and further with a glass powder, if desired, leading to accomplishment of the invention.

Specifically, the dental restorative composition according to this invention has a great characteristic in using a novel organic-inorganic composite filler as the filler. We studied a combination of the viscosity of a matrix monomer constituting the organic-inorganic composite filler with the particle size of the particulate filler. As a result, in case where a matrix monomer having a specific viscosity is selected and kneaded with a particulate filler having a specific particle size, it has been successful in obtaining an organic-inorganic composite filler in which the matrix monomer is mixed without completely wetting the entire surfaces of primary particles of the particulate filler, and in the organic-inorganic filler prepared by polymerizing the kneaded material as it stands, followed by pulverizing, the surface of the inorganic powder is not entirely covered with the resin segment, but the inorganic segment is partially exposed, whereby the resulting organic-inorganic composite filler has a portion having high surface activity.

Further, when this organic-inorganic composite filler is contained in a dental restorative composition, a binding strength to the monomer segment in the dental restorative composition increases, the resulting dental restorative composition is superior in toughness to the dental restorative composition using the conventional inorganic-organic composite filler and becomes a tough material having in particular, a high bending strain energy, resulting to enabling to obtain a restoration which is less in fracture, etc.

Also, since the dental restorative composition according to this invention contains such organic-inorganic composite material, it has a low surface hardness as compared with the conventional dental restorative composition comprising a large amount of the glass powders (a mean particle size: 2 μm or lower) filled therein, and therefore, it has a characteristic that a smooth surface is readily obtained without using a special polishing material.

In addition, we studied the transparency similar to natural teeth, which is an indispensable characteristic to the dental restorative composition. In the resin material, a difference in the refractive index between the particulate filler and the cured matrix monomer caused turbidity inherent to the resin. In this case, it has been found that when the particle size of the particulate filler to be used is controlled to a certain particle size or less, the turbidity inherent to the resin is mitigated, a generally called opalescence can be suppressed.

That is, the dental restorative composition of this invention comprises:

(a) a methacrylate or acrylate monomer, (b) an organic-inorganic composite filler prepared by curing a mixture of a particulate filler having a mean particle size of 20 nm or less with a methacrylate or acrylate monomer having a viscosity of 60 cP or more and pulverizing the cured mixture, (c) a particulate filler having a mean particle size of 20 nm or less, and (d) a polymerization initiator, and further, if desired, (e) a glass powder having a maximum particle size of 5 µm or less and having a mean particle size of from 0.5 to 2 µm.

DETAILED DESCRIPTION OF THE INVENTION

This invention is described below in more detail with respect to each of the constitutional components.

The component (a), methacrylate or acrylate monomer, is a component which is used as a matrix monomer of the dental restorative composition, and also, a monomer having a specific viscosity is a component as a matrix monomer used in order to obtain the component (b), organic-inorganic composite filler.

The methacrylate or acrylate monomer includes various methacrylates or acrylates having an unsaturated double bonds. Specifically, examples of monomers having a viscosity of less than 60 cP include methyl methacrylate, ethyl methacrylate, isopropyl methacrylate, 2-hydroxyethyl methacrylate, 3-hydroxypropyl methacrylate, 2-hydroxy-1, 3-dimethacryloxypropane, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, benzyl methacrylate, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol, trimethacrylate, trimethylolmethane trimethacrylate, pentaerythritol tetramethacrylate, and corresponding acrylates thereto. Examples of monomers having a viscosity of 60 cP or more include 2,2-bis(methacryloxyphenyl)propane, 2,2-bis[4-(2-hydroxy-3-methacryloxypropoxy)phenyl]propane, 2,2-bis(4-methacryloxy-diethoxyphenyl)propane, 2,2-bis(4-methacryloxypolyethoxy-phenyl)propane, di-2-methacryloxyethyl-2,2,4-trimethylhexa-methylene dicarbamate, and corresponding acrylates thereto; methacrylates or acrylates having a urethane bond in the molecule thereof; and other methacrylates or acrylates having a urethane bond. These methacrylates or acrylates are known as the dental material and are used singly or in admixture when the occasion demands.

A suitable amount of the monomer to be compounded, when it is used as the matrix monomer as the component (a) of the dental restorative composition, is from 15 to 40% by weight based on the whole of the dental restorative composition. When the amount of the monomer to be compounded is less than 15% by weight, the amount of the matrix monomer to be compounded is low, so that the kneading operability tends to be inferior. On the other hand, when it exceeds 40% by weight, the amount of the filler is small, so that the polymerization shrinkage tends to be large.

Also, in case when the monomer is used as the matrix monomer for obtaining the component (b), organic-inorganic composite filler, a monomer having a viscosity of 60 cP or more is used singly, or it is used in combination with other monomers, thereby adjusting the viscosity at 60 cP or more. In case where a monomer having a viscosity of less than 60 cP is used, the amount of the inorganic segment on the surface of the organic-inorganic composite filler decreases, so that the activity is low. As a result, in case of preparing the dental restorative composition, the organic-inorganic composite filler fails in bonding to the matrix monomer as the component (a) and is inferior in physical properties. In particular, it is low in bending strain energy to show brittle properties and hence, it is not suitable. On the other hand, when the viscosity of the monomer is too high, the mixing with the component (c) particulate filler, tends to be difficult. Accordingly, it is preferable that the viscosity of the monomer is at 30,000 cP or less. It is suitable that the matrix monomer used in order to obtain the component (b), organic-inorganic composite filler, is contained in an amount of 50~90% by weight in the organic-inorganic composite filler. When the amount of this matrix monomer exceeds 90% by weight, the amount of the inorganic segment portion on the surface of the organic-inorganic composite filler decreases, so that the activity is low. As a result, the organic-inorganic composite filler fails in bonding to the matrix monomer as the component (a) and the dental restorative composition is inferior in physical properties. On the.other hand, when it is less than 50% by weight, the mixing with the inorganic segment as the particulate filler tends to be difficult.

The particulate filler having a mean particle size of 20 nm or less, which is used for the component (b), organic-inorganic composite filler, in combination with the above-described monomer is a component which is used also as the component (c), particulate filler having a mean particle size of 20 nm or less. As this particulate filler, silica such as colloidal silica produced by spray heat decomposition of, e.g., a silane compound is usually used. Besides, alumina, zinc oxide, zirconia, magnesia, titania, and the like may also be used. In case where a particulate powder having a mean particle size of greater than 20 nm is used, the dental restorative composition causes turbidity inherent to the resin to become strong in opalescence, whereby the resulting restoration is inferior in esthetics as compared with natural teeth. Accordingly, such is not suitable. In case where this particulate filler is used as the component (b), organic-inorganic composite filler, it is preferably compounded in an amount of 10~50% by weight in the organic-inorganic composite filler. When the amount of the particulate filler to be compounded is less than 10% by weight, the characteristics as the organic-inorganic composite filler are not sufficiently exhibited. On the other hand, when it exceeds 50% by weight, the kneading with the monomer is hardly carried out. In case where this particulate filler is used as the component (c), particulate filler having a mean particle size of 20 nm or less, it is preferably used in an amount of 1~20% by weight based on the whole of the dental restorative composition. When the amount of the particulate filler to be compounded is less than 1% by weight, the effect is not sufficiently exhibited, whereas when it exceeds 20% by weight, the amount of the monomer is too much, whereby the physical properties of the resulting restoration tend to be lowered. Incidentally, the particulate filler having a mean particle size of 20 nm or less, which is used as the component (c), is also effective for preventing the liquid separation of the dental restorative composition.

The component (b), organic-inorganic composite filler, is prepared by mixing the above-described methacrylate or acrylate having a viscosity of 60 cP or more and the particulate filler having a means particle size of 20 nm or less and curing the mixture, followed by pulverizing. During this time, as a curing agent to be used for polymerizing in the monomer, in case of heat-polymerization, an organic peroxide, an azo compound, or the like is mixed, and in case of photo-polymerization, a photo-polymerization initiator is used, respectively. Besides, the curing can be achieved by chemical-polymerization. Accordingly, the method for curing the mixture is not particularly limited. Specifically, an analogous substance to. the component (d), polymerization initiator, as described below, which cures the dental restorative composition per se, can be used. It is preferred that the organic-inorganic composite filler has a mean particle size of 5~50 μm and is compounded in an amount of 10~70% by weight based on the whole of the dental restorative composition. When the amount of the organic-inorganic composition filler to be compounded is less than 10% by weight, the effect added to the organic-inorganic composite filler is not sufficiently exhibited. On the other hand, when it exceeds 70% by weight, the binding between the component (b), organic-inorganic composite filler, and the component (a), matrix monomer, is weak, whereby the physical properties tend to be lowered.

The component (d), polymerization initiator, is properly selected and added according to the type of polymerization for which the dental restorative composition is used.

In case where the dental restorative composition is of a heat-polymerization type, as the polymerization initiator are mainly used organic peroxides or azo compounds. As the organic peroxides are preferred diacyl peroxides having an aromatic ring or peroxy esters which are considered to be an ester of perbenzoic acid. Specific examples include benzoyl peroxide, 2,4-dichlorobenzoyl peroxide, m-tolyl peroxide, t-butyl peroxybenzoate, di-t-butyl peroxyisophthalate, 2,5-dimethyl-2,5-di(benzoylperoxy)hexane, and 2,5-dimethyl-2,5-di{(o-benzyl)benzoylperoxy}hexane. Also, azo compounds such as azobisisobutyronitrile or organometallic compounds such as tributylborone can be used.

In case where the dental restorative composition is of a chemical-polymerization type, as the polymerization initiator are exemplified combinations of an organic peroxide with an aromatic tertiary amine. These compounds are used in such a manner that the organic peroxide is compounded in one paste, whereas the aromatic tertiary amine is compounded in another paste. Like the organic peroxide which is used for the polymerization initiator of a heat-polymerization type as described above, diacyl peroxides having an aromatic ring or peroxy esters which are considered to be an ester of perbenzoic acid are preferred. Specific examples include benzoyl peroxide, 2,4-dichlorobenzoyl peroxide, m-tolyl peroxide, t-butyl peroxybenzoate, di-t-butyl peroxyisophthalate, 2,5-dimethyl-2,5-di(benzoylperoxy)hexane, and 2,5-dimethyl-2,5-di{(o-benzyl)benzoylperoxy}hexane. As the aromatic tertiary amine are preferred tertiary amines in which a nitrogen atom is directly substituted on the aromatic group. Specific examples include N,N-dimethyl-p-toluidine, N,N-dimethylaniline, N-methyl-N-β-hydroxyaniline, N,N-di(β-hydroxyethyl)-aniline, N,N-di(β-hydroxyethyl)-p-toluidine, N,N-di(β-hydroxypropyl)-aniline, N,N-di(β-hydroxypropyl)-p-toluidine, ethyl N,N-dimethylaminobenzoate, and isoamyl N,N-dimethylaminobenzoate.

In case where the dental restorative composition is of a photo-polymerization type, as the photo-polymerization initiator are usually used in combinations of a sensitizer with a reducing agent. Examples of the sensitizer which can be used include camphorquinone, benzyl, diacetyl, benzyl dimethyl ketal, benzyl diethyl ketal, benzyl di(2-methoxyethyl) ketal, 4,4'-diemthylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthi-oxanthone, thioxanthone-10,10-dioxide, thioxanthone-10-oxide, benzoinmethyl ether, benzoinethyl ether, isopropyl ether, benzoinbutyl ether, benzophenone, bis(4-dimethyl-aminophenyl)ketone, 4,4,-bisdiethylamino benzophenone, acyl phosphine oxide derivatives, and azide group-containing compounds. The compounds are used singly or in admixture of two or more thereof.

As the reducing agent are usually used tertiary amines and the like. As the tertiary amines are preferred N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate. As other reducing agents are exemplified benzoyl peroxide, sodium sulfinate derivatives, and organometallic compounds.

Needless to say, the respective heat-polymerization type, chemical-polymerization type and photo-polymerization type polymerization initiators as described above can be used in combination.

In the case of the dental restorative composition of a photo-polymerization type, the polymerization reaction is achieved by irradiation with rays such as ultraviolet light or visible light. Examples of light sources which can be used include various mercury vapor lamps of a ultrahigh pressure, a high pressure, a medium pressure, or a low pressure, a chemical lamp, a carbon arc lamp, a metal halide lamp, a fluorescent lamp, a tungsten lamp, a xenone lamp, and an argon ion laser.

In addition, although the component (e), glass powder having a maximum particle size of 5 μm or less and having a mean particle size of from 0.5 to 2 μm, which is compounded, if desired, is not particularly limited so far as it has a composition for forming the glass, an aluminosilicate glass is mainly used. It can be prepared by melting a raw material selected from silica, alumina, feldspar, kaolin, aluminum hydroxide, aluminum silicate, mullite, calcium silicate, strontium silicate, sodium silicate, aluminum carbonate, calcium carbonate, strontium carbonate, sodium carbonate, sodium fluoride, calcium fluoride, aluminum fluoride, strontium fluoride, sodium phosphate, calcium phosphate, aluminum phosphate, strontium phosphate, and other titanium salts and barium salts, and cooling then pulverizing. In case where an alkaline earth metal such as calcium, strontium, and barium is used in the composition of the glass powder, since it can impart X-ray contrast properties to the dental restorative composition, it is preferable from the clinical viewpoint. When a glass powder having a maximum particle size of 5 μm or less and having a mean particle size of from 0.5 to 2 μm is used, restorations having superior surface smoothness can be obtained. On the other hand, when a glass powder having a maximum particle size of more than 5 μm and having a mean particle size of more than 2 μm is used, the resulting restoration fails in surface smoothness, whereas when the mean particle size is less than 0.5 μm, turbidity inherent to the resin is generated, and much opalescence appears, whereby the esthetics tends to be inferior. It is preferred that the glass powder is added in an amount of from 5 to 60% by weight based on the whole of the dental restorative composition, if desired.

If further desired, the dental restorative composition according to this invention may contain trace amounts of an ultraviolet absorbing agent, a coloring agent, a polymerization inhibitor, a discoloration-preventing agent, an antibacterial agent, and the like.

The dental restorative composition according to this invention is described specifically with reference to the following Examples. The methacrylate or acrylate monomers, which were used as the component (a) and the component (b) in the Examples and Comparative Examples, are abbreviated as follows.

UDMA: Di-2-methacryloxyethyl-2,2,4-trimethylhexamethylene dicarbamate
3G: Triethylene glycol dimethacrylate
BG: 1,3-Butanediol dimethacrylate
TMPT: Trimethylolpropane trimethacrylate
NPG: Neopentyl glycol dimethacrylate
Bis-GMA: 2,2-Bis[4-(2-hydroxy-3-methacryloxypropoxy)-phenyl]propane
Bis-MPEPP: 2,2-Bis(4-methacryloxypolyethoxyphenyl) propane
THF: Tetrahydrofurfuryl methacrylate As the particulate fillers used as the component (a) and the component (b) were used colloidal silicas (trade names: Aerosil R972, Aerosil 200, Aerosil 380, and Aerosil 50, made by Nippon Aerosil Corp). The mean particle sizes of the particulate fillers are 16 nm for Aerosil R972, 12 nm for Aerosil 200, 7 nm for Aerosil 380, and 30 nm for Aerosil 50, respectively.

In addition, the organic-inorganic composite filler was prepared in the following manner. While the following organic-inorganic composite fillers A to D are those falling within the scope of the claims for patent of this invention, the organic-inorganic composite fillers E and F are those prepared for the Comparative Examples, falling outside the scope of the claims for patent of this invention (the organic-inorganic composite filler E falls outside the claimed scope in terms of the viscosity of the monomer, and the organic-inorganic composite filler F falls outside the claimed scope in terms of the mean particle size of the particulate filler).

Organic-inorganic composite filler A:

| | |
|---|---|
| Mixed solution (monomer viscosity: 80 cP) of UDMA and 3G (weight ratio: 3/7) containing 1% by weight of azobisisobutyronitrile | 70% by weight |
| Aerosil 200 (mean particle size: 12 nm) | 30% by weight |

A mixture of the above components was thermally cured and pulverized into a mean particle size of 10 μm.

Organic-inorganic composite filler B:

| | |
|---|---|
| Mixed solution (monomer viscosity: 103 cP) of UDMA and NPG (weight ratio: 7/3) containing 1% by weight of azobisisobutyronitrile | 70% by weight |
| Aerosil R972 (mean particle size: 16 nm) | 30% by weight |

A mixture of the above components was thermally cured and pulverized into a mean particle size of 15 μm.

Organic-inorganic composite filler C:

| | |
|---|---|
| Mixed solution (monomer viscosity: 1,020 cP) of Bis-MPEPP containing 1% by weight of azobisisobutyronitrile | 60% by weight |
| Aerosil R972 (mean particle size: 16 nm) | 40% by weight |

A mixture of the above components was thermally cured and pulverized into a mean particle size of 15 μm.

Organic-inorganic composite filler D:

| | |
|---|---|
| Mixed solution (monomer viscosity: 1,020 cP) of Bis-MPEPP containing 1% by weight of azobisisobutyronitrile | 60% by weight |
| Aerosil R972 (mean particle size: 16 nm) | 40% by weight |

A mixture of the above components was thermally cured and pulverized into a mean particle size of 8 μm.

Organic-inorganic composite filler E:

| | |
|---|---|
| Mixed solution (monomer viscosity: 57 cP) of TMPT containing 1% by weight of azobisisobutyronitrile | 70% by weight |
| Aerosil R972 (mean particle size: 16 nm) | 30% by weight |

A mixture of the above components was thermally cured and pulverized into a mean particle size of 15 μm.

Organic-inorganic composite filler F:

| | |
|---|---|
| Mixed solution (monomer viscosity: 103 cP) of UDMA and NPG (weight ratio: 7/3) containing 1% by weight of azobisisobutyronitrile | 70% by weight |
| Aerosil 50 (mean particle size: 30 nm) | 30% by weight |

A mixture of the above components was thermally cured and pulverized into a mean particle size of 15 µm.

As the glass powder, the following glass powders were used.

Glass powder A: Aluminosilicate glass powder (mean particle size: 0.9 µm, maximum particle size: 2.5 µm)

Glass powder B: Aluminosilicate glass powder (mean particle size: 2.0 µm, maximum particle size: 5.0 µm)

Glass powder C: Strontium glass powder (mean particle size: 0.5 µm, maximum particle size: 1.5 µm)

EXAMPLE 1

(a) Methacrylate or acrylate monomer: UDMA 20% by weight & 3G 10% by weight

[The component (d), photo-polymerization initiator, was prepared by dissolving 0.5 parts by weight of camphorquinone as the photo-sensitizer and 1 part by weight of dimethylaminoethyl methacrylate as the reducing agent based on 100 parts by weight of the whole of the above-described monomer solution.]

(b) Organic-inorganic composite filler B: 20% by weight
(c) Particulate filler, Aerosil R972: 5% by weight
(e) Glass powder A: 45% by weight These components were mixed by a kneader in a dark room to obtain a dental restorative composition in a paste form. The thus obtained dental restorative composition was subjected to various tests as described later. The results obtained are shown in Table 1.

EXAMPLES 2 to 9

Following the same procedures as in Example 1, dental restorative compositions having a composition and compounding amounts as shown in Table 1 were prepared. The thus prepared dental restorative compositions were subjected to the same tests as in Example 1. The results are shown in Table 1.

In these Examples, the photo-polymerization initiator in the monomer was the same as in Example 1.

EXAMPLE 10

This Example is concerned with a case where it is not necessary to consider the polymerization shrinkage and is an example of an application to artificial teeth in which in particular, the manufacture side performs the curing. In this Example, the component (e), glass powder, is not compounded.

(a) Methacrylate or acrylate monomer: UDMA 30% by weight and 3G 10% by weight

[The component (d), polymerization initiator, was prepared by dissolving 1 part by weight of azobisisobutyronitrile based on 100 parts by weight of the whole of the above-described monomer solution.]

(b) Organic-inorganic composite filler C: 50% by weight
(c) Particulate filler, Aerosil R972: 10% by weight These components were mixed by a kneader in a dark room to obtain a dental restorative composition in a paste form. The thus obtained dental restorative composition was subjected to the same tests as in Example 1. In the curing method of the test specimen, the curing was carried out at 100° C. while applying a pressure (500 kg/cm$^2$) by the dry heat-curing method. The results obtained are shown in Table 1.

COMPARATIVE EXAMPLE 1

A dental restorative composition containing a quartz glass powder, which is generally called as a conventional type, was tested. A quartz glass powder having a maximum particle size of 50 µm and having a mean particle size of 20 µm in terms of a glass powder was used and named a glass powder D. The tests were carried out in the same manner as in Examples 1 to 10, while employing the composition and compounding amounts as shown in Table 2. The results are shown in Table 2. The dental restorative composition of this Comparative Example was inferior to those of Examples 1 to 10 in all of the test items.

COMPARATIVE EXAMPLE 2

A dental restorative composition using only a particulate filler was subjected to the same tests as in Examples 1 to 10, while employing the composition and compounding amounts as shown in Table 2. The results are shown in Table 2. Though the dental restorative composition of this Comparative Example was good in the transparency, the polishing workability, and the surface smoothness, it was inferior to those of Examples 1 to 10 in other test items.

COMPARATIVE EXAMPLE 3

As an example of the recent. dental restorative composition was prepared a dental restorative composition using a filler composed mainly of a glass powder having a maximum particle size of approximately 2 µm. The thus prepared dental restorative composition was subjected to the same tests as in Examples 1 to 10, while employing the composition and compounding amounts as shown in Table 2. The results are shown in Table 2. The dental restorative composition of this Comparative Example was inferior to those of Examples 1 to 10 in the polishing workability and the bending strain energy.

COMPARATIVE EXAMPLE 4

This Comparative Example is concerned with an example of the dental restorative composition in which the viscosity of the monomer constituting the organic-inorganic composite filler is lower than that as in the claimed scope. The dental restorative composition of this Comparative Example was subjected to the same tests as in Examples 1 to 10, while employing the composition and compounding amounts as shown in Table 2. The results are shown in Table 2. This dental restorative composition was inferior to those of Examples 1 to 10 in the bending strength and the bending strain energy.

COMPARATIVE EXAMPLE 5

This Comparative Example is concerned with an example of the dental restorative composition in which the particle size of the filler constituting the organic-inorganic composite filler is greater than that as in the claimed scope. The dental restorative composition of this Comparative Example was subjected to the same tests as in Examples 1 to 10, while employing the composition and compounding amounts as shown in Table 2. The results are shown in Table 2. This dental restorative composition was inferior to those of Examples 1 to 10 in the bending strength, the bending strain energy, and the transparency.

COMPARATIVE EXAMPLE 6

This Comparative Example is concerned with an example of the dental restorative composition in which the particle size of the glass powder is greater than that as in the claimed scope.

As a glass powder E was prepared an aluminosilicate glass having a maximum particle size of 15 $\mu$m and having a mean particle size of 7 $\mu$m. The dental restorative composition of this Comparative Example was subjected to the same tests as in Examples 1 to 10, while employing the composition and compounding amounts as shown in Table 2. The results are shown in Table 2. This dental restorative composition was inferior to those of Examples 1 to 10 in the polishing workability and the surface smoothness.

COMPARATIVE EXAMPLE 7

This Comparative Example is concerned with an example of the dental restorative composition in which the particle size of the particulate filler (Aerosil 50, particle size: 30 nm) is greater than that as in the claimed scope. The dental restorative composition of this Comparative Example was subjected to the same tests as in Examples 1 to 10, while employing the composition and compounding amounts as shown in Table 2. The results are shown in Table 2. This dental restorative composition was inferior to those of Examples 1 to 10 in the transparency.

The respective tests were carried out in the following manners.

(1) Bending strength and bending strain energy:

The dental restorative composition to be tested was filled in a mold of 2 mm×2 mm×25 mm and brought into press contact with a glass sheet via cellophane, and the both surfaces of the sample were irradiated with a light by a visible ray irradiator (a trade name: LABOLIGHT LV-II, manufactured by GC Corporation) for 3 minutes. The resulting sample was immersed in water for 24 hours and subjected to a three-point bending test at a span of 20 mm and at a crosshead speed of 1 mm/min. by a testing machine (a trade name: Autograph, manufactured by Shimadzu Corporation).

The number of samples was five, and average values of the bending strength and of the bending strain energy were obtained from the maximum stress and the area of the stress strain curve of the chart, respectively.

(2) Transparency:

The dental restorative composition to be tested was filled in a mold having an inside diameter of 20 mm and a thickness of 1 mm and brought into press contact with a glass sheet via cellophane, and the both surfaces of the sample were irradiated with a light by a visible ray irradiator (a trade name: LABOLIGHT LV-II, manufactured by GC Corporation) for 3 minutes. The resulting sample was polished with an emery paper #600, a water paste of polishing sand (fine) for dental technology, and a water paste of alumina (0.3 $\mu$m) for finishing in this order, thereby finishing it into a thickness of (1.00±0.01) mm. A light (a trade name: Sunream, manufactured by Daiwa Light K.K.) was irradiated at a distance of 1 m on the sample surface direction. A photodiode array type spectrophotometer (a trade name: Spectrascan PR650, manufacture by Photo Research Co., Ltd.) was used as a photometry meter, and a center of $\phi$3 mm of the sample surface on a light trap or standard white board (magnesium oxide) was measured at 45° to the sample surface direction. The L* (black) and L* (white) values in the CIE-L*a*b* color specification system were calculated, whereby $\Delta L = L^*$ (white)–L* (black) was taken as an index. With respect to the transparency required for the dental restorative, values of 22 or more may be sufficient as the value necessary for the enamel of a natural tooth, etc.

(3) Polishing properties:

The dental restorative composition to be tested was filled in a mold having an inside diameter of 20 mm and a thickness of 2 mm and brought into press contact with a glass sheet via cellophane, and the both surfaces of the sample were irradiated with a light by a visible ray irradiator (a trade name: LABOLIGHT LV-II, manufactured by GC Corporation) for 3 minutes. One surface of the resulting sample was once roughed by a tungsten carbide bar and then polished in the customary manner. The polishing workability and the surface smoothness by visual observation were evaluated on five criteria as described below.

5: Good
4: Slightly good
3: Moderate
2: Slight bad
1: Bad

TABLE 1

| | Composition | | | | | | Physical properties of restorative | | | | |
| | Methacrylate or acrylate monomer (weight %) | | Organic-inorganic composite (weight %) | | Glass powder (weight %) | | Particulate filler (weight %) | | Bending strength (MPa) | Bending strain energy (MPa) | Transparency ($\Delta$L) | Polishing properties | |
| | | | | | | | | | | | | Workability | Surface smoothness |
|---|---|---|---|---|---|---|---|---|---|---|---|---|---|
| Example 1 | UDMA | 25 | B | 20 | A | 45 | R972 | 5 | 145 | 2.01 | 36 | 5 | 5 |
| | 3G | 5 | | | | | | | | | | | |
| Example 2 | UDMA | 20 | A | 10 | A | 55 | R972 | 5 | 150 | 1.98 | 35 | 5 | 5 |

TABLE 1-continued

| | Composition | | | | | | | Physical properties of restorative | | | Polishing properties | |
|---|---|---|---|---|---|---|---|---|---|---|---|---|
| | Methacrylate or acrylate monomer (weight %) | | Organic-inorganic composite (weight %) | | Glass powder (weight %) | | Particulate filler (weight %) | | Bending strength (MPa) | Bending strain energy (MPa) | Transparency (ΔL) | Workability | Surface smoothness |
| Example 3 | BG<br>UDMA<br>3G | 10<br>20<br>5 | C | 67 | B | 5 | R972 | 3 | 139 | 2.25 | 42 | 5 | 5 |
| Example 4 | UDMA<br>3G | 15<br>15 | C | 18 | B | 50 | R972 | 2 | 147 | 1.95 | 32 | 5 | 5 |
| Example 5 | UDMA<br>3G<br>NPG | 15<br>10<br>5 | A | 30 | A<br>B | 10<br>20 | R972 | 15 | 158 | 2.21 | 40 | 5 | 5 |
| Example 6 | Bis-GMA<br>3G | 10<br>15 | D | 20 | C | 50 | R972 | 5 | 144 | 2.05 | 30 | 5 | 5 |
| Example 7 | Bis-MPEPP<br>BG | 20<br>10 | D | 40 | C | 25 | R972 | 5 | 148 | 2.09 | 31 | 5 | 5 |
| Example 8 | UDMA<br>THF | 15<br>5 | A<br>B | 30<br>5 | B | 40 | R972 | 5 | 151 | 2.11 | 39 | 5 | 5 |
| Example 9 | UDMA<br>BG | 30<br>10 | A | 20 | A | 30 | R972 | 10 | 138 | 2.28 | 35 | 5 | 5 |
| Example 10 | UDMA<br>3G | 30<br>10 | C | 50 | | | R972 | 10 | 163 | 2.55 | 45 | 5 | 5 |

TABLE 2

| | Composition | | | | | | | Physical properties of restorative | | | Polishing properties | |
|---|---|---|---|---|---|---|---|---|---|---|---|---|
| | Methacrylate or acrylate monomer (weight %) | | Organic-inorganic composite (weight %) | | Glass powder (weight %) | | Particulate filler (weight %) | | Bending strength (MPa) | Bending strain energy (MPa) | Transparency (ΔL) | Workability | Surface smoothness |
| Comparative Example 1 | Bis-GMA<br>3G | 10<br>5 | | | D | 80 | R972 | 5 | 108 | 0.81 | 20 | 2 | 1 |
| Comparative Example 2 | Bis-MPEPP | 70 | | | | | R972 | 30 | 68 | 1.2 | 40 | 5 | 5 |
| Comparative Example 3 | Bis-GMA<br>3G | 10<br>3 | | | C | 82 | R972 | 5 | 134 | 0.75 | 30 | 2 | 4 |
| Comparative Example 4 | UDMA<br>3G | 25<br>5 | E | 20 | A | 45 | R972 | 5 | 113 | 0.85 | 37 | 5 | 5 |
| Comparative Example 5 | UDMA<br>3G | 25<br>5 | F | 20 | A | 45 | R972 | 5 | 120 | 0.79 | 18 | 5 | 5 |
| Comparative Example 6 | UDMA<br>3G | 25<br>5 | B | 20 | E | 45 | R972 | 5 | 130 | 1.92 | 25 | 4 | 2 |
| Comparative Example 7 | UDMA<br>BG | 30<br>10 | A | 20 | A | 30 | Aerosil<br>R972 | 50<br>10 | 139 | 2.19 | 19 | 5 | 5 |

As described above in detail, the dental restorative composition according to this invention is a dental restorative composition from which restorations having superior surface smoothness and transparency similar to natural teeth, having superior bending strength and bending strain energy characteristics, and being provided with easy polishing properties can be realized, an aspect which has never been attained by the conventional dental restorative compositions, through a combination of a novel organic-inorganic composite filler with a particulate filler as the filler to be used. The dental restorative composition according to this invention can be widely applied to dental filling material, crown restoratives, restoratives for bridges, inlays, onlays, outer caps, artificial teeth, resin teeth, ceramics teeth, crown resins fixing cement, and repair of crown ceramics and materials for other prosthesis, conservative and preventive material. Accordingly, this invention greatly contributes to the dental remedy.

While the invention has been described in detail and with reference to specific embodiments thereof, it will be apparent to one skilled in the art that various changes and modifications can be made therein without departing from the spirit and scope thereof.

What is claimed is:
1. A dental restorative composition comprising:
 (a) a methacrylate or acrylate monomer,
 (b) an organic-inorganic composite filler prepared by curing a mixture of a particulate filler having a mean particle size of 20 nm or less with a methacrylate or acrylate monomer having a viscosity of 60 cP or more and pulverizing the cured mixture, (c) a particulate filler having a mean particle size of 20 nm or less, and (d) a polymerization initiator.

2. A dental restorative composition comprising:

(a) a methacrylate or acrylate monomer, (b) an organic-inorganic composite filler prepared by curing a mixture of a particulate filler having a mean particle size of 20 nm or less with a methacrylate or acrylate monomer having a viscosity of 60 cP or more and pulverizing the cured mixture, (c) a particulate filler having a mean particle size of 20 nm or less, (d) a polymerization initiator, and (e) a glass powder having a maximum particle size of 5 μm or less and having a mean particle size of from 0.5 to 2 μm.

3. A dental restorative composition as claimed in claim 2, wherein the content of the component (e), glass powder having a maximum particle size of 5 μm or less and having a mean particle size of from 0.5 to 2 μm, is from 5 to 60% by weight based on the whole of the dental restorative composition.

4. A dental restorative composition as claimed in any one of claims 1 to 3, wherein the content of the component (a), methacrylate or acrylate monomer, is from 15 to 40% by weight based on the whole of the dental restorative composition.

5. A dental restorative composition as claimed in any one of claims 1 to 3, wherein the content of the component (b), organic-inorganic composite filler prepared by curing a mixture of a particulate filler having a mean particle size of 20 nm or less with a methacrylate or acrylate monomer having a viscosity of 60 cP or more and pulverizing the cured mixture, is from 10 to 70% by weight based on the whole of the dental restorative composition.

6. A dental restorative composition as claimed in any one of claims 1 to 3, wherein in the component (b), organic-inorganic composite filler prepared by curing a mixture of a particulate filler having a mean particle size of 20 nm or less with a methacrylate or acrylate monomer having a viscosity of 60 cP or more and pulverizing the cured mixture, the content of the particulate filler having a mean particle size of 20 nm or less is from 10 to 50% by weight based on the component (b).

7. A dental restorative composition as claimed in any one of claims 1 to 3, wherein the component (b), organic-inorganic composite filler prepared by curing a mixture of a particulate filler having a mean particle size of 20 nm or less with a methacrylate or acrylate monomer having a viscosity of 60 cP or more and pulverizing the cured mixture, has a mean particle size of from 5 to 50 μm.

8. A dental restorative composition as claimed in any one of claims 1 to 3, wherein the content of the component (c), particulate filler having a mean particle size of 20 nm or less, is from 1 to 20% by weight based on the whole of the dental restorative composition.

* * * * *